United States Patent [19]
Snyder et al.

[11] 4,027,538
[45] June 7, 1977

[54] LATCH RELEASING MECHANISM FOR WATER SAMPLERS

[75] Inventors: Robert P. Snyder, Bay City; Edmund P. Deja, Saginaw, both of Mich.

[73] Assignee: Trippensee Corporation, Saginaw, Mich.

[22] Filed: Feb. 9, 1976

[21] Appl. No.: 656,535

[52] U.S. Cl. .......................................... 73/425.4 R
[51] Int. Cl.² .......................................... G01N 1/10
[58] Field of Search ........ 73/425.4 R, 421 R, 425.2

[56] References Cited
UNITED STATES PATENTS

| | | | |
|---|---|---|---|
| 3,277,723 | 10/1966 | Bodman et al. | 73/425.4 R |
| 3,841,162 | 10/1974 | Duperon | 73/425.4 R |

*Primary Examiner*—Donald O. Woodiel
*Attorney, Agent, or Firm*—Learman & McCulloch

[57] ABSTRACT

A Kemmerer style water sampler has a tubular body open at both ends and through which extends a connecting rod. The lower end of the connecting rod is fixed to a closure for the lower end of the body. The upper end of the connecting rod is releasably latched to an upper closure and carries a latch member which is engageable by and disengageable from a pair of clasp members mounted on the upper closure for movements in directions into and out of latching position. Each clasp member is provided with an upstanding motion transmitting member having inclined, confronting surfaces spaced apart to provide a chamber. Reciprocably accommodated in the chamber is an operating member that is tapered complementally to the inclination of the surfaces of the motion transmitting members so that movement of the operating member axially in one direction effects movement of the clasp members out of latching engagement with the latch member, thereby enabling the upper and lower closures to seal the opposite ends of the body.

18 Claims, 6 Drawing Figures

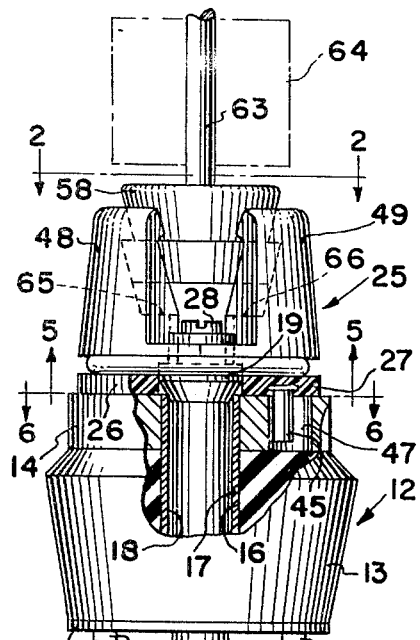
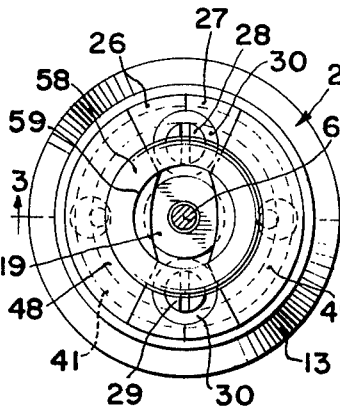
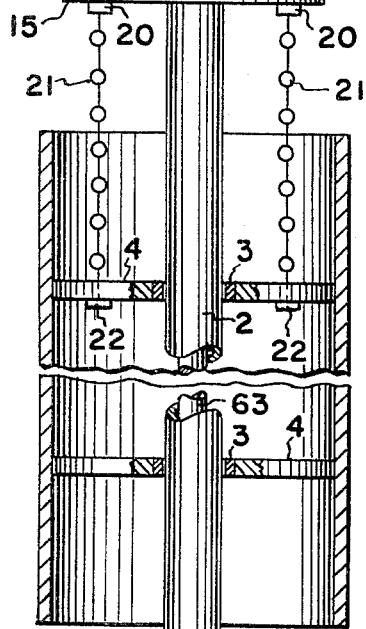
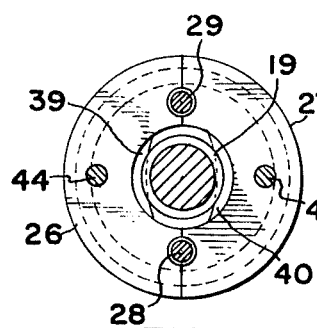
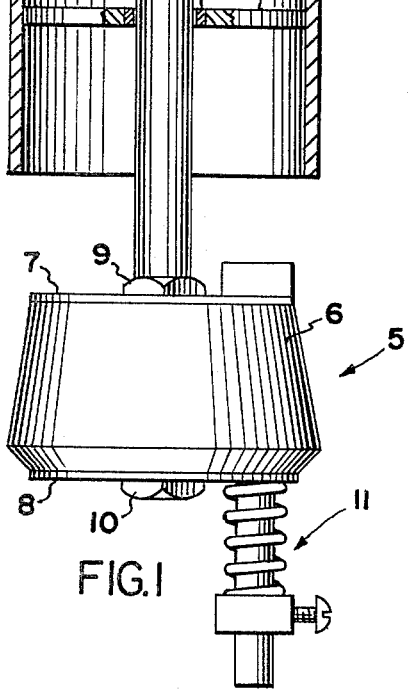
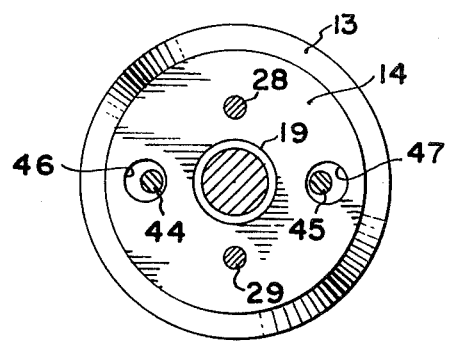

LATCH RELEASING MECHANISM FOR WATER SAMPLERS

The invention disclosed herein relates to a remotely controlled latch releasing mechanism for effecting the closing of opposite ends of a normally open water sampling tube of the kind which may be lowered to a known depth in a body of water at which time the ends of the tube may be sealed so as to entrap a sample of water taken at the known depth. Sampling devices of the kind to which the invention relates conventionally are known as Kemmerer style water samplers.

A Kemmerer style water sampler of the kind to which the invention relates is disclosed in U.S. Pat. No. 3,841,162 granted Oct. 15, 1974. The apparatus disclosed in that patent comprises an open ended, tubular body having top and bottom closures which initially are latched in positions spaced from the ends of the tubular body, but which are adapted to close the ends of the tubular body in response to remote operation of a latch release mechanism. Although the latch release mechanism incorporated in the patented construction has several advantages over preexisting mechanisms, continued development has resulted in the mechanism disclosed herein and which incorporates several improvements over the patented construction.

In the operation of Kemmerer style water samplers heretofore, it has been the practice to effect unlatching of the closure latching mechanism by dropping a weighted messenger and guiding it during its movement so that it enters a space between a pair of upstanding ears carried by separable clasp plates. Movement of the messenger between the ears wedges the ears apart so as to move the clasp plates out of latching engagement with the latch. In such a construction it is rare that the wedging thrust on the ears is equal. Instead, one ear or the other absorbs the initial impact of the messenger. Although the arrangement is such that the force of the messenger ultimately is transferred to the other ear as well, some finite period of time is required for such transfer to occur. As a consequence, release of the latch is not as fast as it could be if the force of the messenger were transmitted to both ears simultaneously.

Rapid movement of both clasp plates toward their unlatching position is highly desirable, particularly in those instances in which the axis of the water sampler is inclined to the vertical due to the effect of a current in the body of water in which the sampler is suspended. When the axis of the sampler is so inclined, the speed of movement of the messenger is less than it would be if the messenger falls vertically. Thus, less force is available to effect unlatching of the latch mechanism and it is possible that so much energy may be absorbed by one of the ears that insufficient energy will be available to effect full unlatching of the clasp plate associated with the other ear.

In view of the likelihood that the initial force of the messenger will be absorbed by one of the unlatching ears, rather than by both, it has been the practice heretofore to construct the ears of metal so as to guard against breaking of the ears. The use of metal, however, has certain well known disadvantages when subjected to repeated immersions in either fresh or salt water unless the metal is stainless steel or is especially treated to be corrosion resistant. In either case, the use of metal adds to the expense of the sampler and increases its weight.

The foregoing disadvantages are overcome in the construction disclosed herein by incorporating an axially movable operating member between a pair of spaced apart motion transmitting members which form integral parts of the clasp members, the operating member and the motion transmitting members being complementally tapered and the operating member being mounted in a position to be engaged by a messenger so as to exert equal and simultaneous thrust on both motion transmitting members and thereby effect rapid and simultaneous movement of the clasp members toward their unlatching positions. The improved construction makes it possible to use materials other than metal for the motion transmitting means.

Apparatus constructed in accordance with a preferred embodiment of the invention is disclosed in the accompanying drawings wherein:

FIG. 1 is an elevational view, partly in section, of a Kemmerer style water sampler having latch releasing mechanism constructed according to the invention, the closures of the sampler being latched in open position;

FIG. 2 is a sectional view taken on the line 2—2 of FIG. 1;

FIG. 3 is a sectional view taken on the line 3—3 of FIG. 2, but illustrating the latch releasing mechanism in released position;

FIG. 4 is a sectional view taken on the line 4—4 of FIG. 3; and

FIGS. 5 and 6 are sectional views taken on the lines 5—5 and 6—6, respectively, of FIG. 1.

Apparatus constructed in accordance with the invention is adapted for use in conjunction with a water sampler of the Kemmerer type having a cylindrical, tubular body 1 open at both ends. Extending coaxially through the body 1 is a hollow connecting rod 2 which is slideably supported by bearings 3 carried by spider-like supports 4 that are welded or otherwise suitably fixed to the interior of the body. The rod 2 has a considerably greater length than that of the body 1 and is fixed at one end to a closure 5 comprising a truncated conical member 6 formed of rubber or rubbery material sandwiched between metallic plates 7 and 8. The rod extends through aligned opening secured in the members 6, 7, and 8 and is fixed with respect thereto by nuts 9 and 10. An outlet 11 of conventional construction also is incorporated in the closure 5 for the purpose of permitting the contents of the body 1 to be drained when desired.

The sampler also includes an upper closure 12 having a truncated conical body 13 formed of rubber or rubbery material sandwiched between an upper support plate 14 and a lower plate 15. The body 13 is provided with a bore 16 within which is a sleeve 17, the sleeve being secured to the upper and lower plates 14 and 15, respectively. The support plate 14 has an opening 18 and the plate 15 has a similar opening (not shown) through which the connecting rod 2 slideably extends.

The upper end of the connecting rod 2 is provided with an enlargement or latch part 19 of greater diameter than that of the sleeve 17 and the opening 18, and the enlargement 19 is located above the upper end of the sleeve 17 so as to prevent movement of the closure 12 off the upper end of the rod 2. The closure 12, however, is capable of sliding movement along the rod toward the opposite or lower closure 5.

The lower plate 15 is provided with anchor lugs 20 to which corresponding ends of tether chains 21 are fixed, the opposite ends of the chains being fixed to anchor members 22 carried by the upper support 4. The chains 21 limit movement of the closure 12 in a direction away from the adjacent end of the body 1, but permit movement of the closure toward the body so as to enable the closure to seat on and seal the adjacent or upper end of the body 1.

Except for the support plate 14, the apparatus thus far described corresponds to that disclosed in the aforementioned U.S. Pat. No. 3,841,162 and forms no part of the invention per se, aside from the manner in which it cooperates with apparatus yet to be described.

Latch release mechanism constructed according to the invention is designated generally by the reference character 25 and comprises a pair of segment-shaped clasp members 26 and 27 mounted atop the plate 14 for reciprocating movements toward and away from one another into and out of latching engagement with the latch 19. The clasp members 26 and 27 are mounted by means of headed screws 28 and 29 carried by the plate 14 in diametrically opposed positions, the heads of the screws projecting above the level of the members 26 and 27 so as to permit the latter to be accommodated between the plate 14 and the heads of the screws. Preferably, washers 30 are interposed between the screw heads and the clasp members and rest atop the clasp members.

The clasp members 26 and 27 have confronting edges 31 and 32, respectively, which are adapted to abut one another. To enable the edges to abut one another, they are provided with semi-circular notches 33 and 34 at their opposite ends for the accommodation of the shanks of the screws 28 and 29. The confronting surfaces 31 and 32 of the clasp members also are notched as at 35 and 36 to provide a recess R of such size as to accommodate the latch member 19 when the non-relieved portions of the edges 31 and 32 of the clasp members abut one another. The confronting surfaces of the clasp members also are notched, as at 37 and 38, to form shoulders 39 and 40 overlying the recess R for a purpose to be explained subsequently.

The clasp members 26 and 27 constantly are biased toward one another and toward their latching positions by an endless garter spring 41 that is accommodated in grooves 42 and 43 formed in the outer surfaces of the clasp members 26 and 27. The clasp members, however, are capable of movement away from one another against the force of the bias spring.

Means is provided to limit movement of the clasp members away from one another and comprises a pin 44 fixed to the clasp 26 and a similar pin 45 fixed to the clasp 27, the pins projecting beyond the lower surfaces of the respective clasp members and being accommodated in openings 46, 47 in the plate 14. The openings 46, 47 are larger in diameter than are the pins 44 and 45 so as to enable the clasp members 26 and 27 to move a limited distance away from one another.

The clasp member 26 includes an upstanding force transmitting member 48 and the clasp member 25 includes a similar force transmitting member 49. The members 48 and 49 are arcuate and have confronting surfaces 50 and 51, respectively, which are inclined to the vertical and are spaced from one another to form therebetween a downwardly tapering chamber 52. Adjacent the free end of each member 48 and 49 is an inwardly directed stop flange 53 and 54, respectively, which overhangs the chamber 52. The free ends of the members 48 and 49 also have inclined surfaces 55 and 56 which, together, form a tapered throat communicating with the chamber 52.

Fitted into the chamber 52 is an operating member 57 comprising an annular body 58 having an axial bore 59 the diameter of which is greater than that of the latch 19 so as to permit the latter to pass through the body. The outer surface of the body 58 has a lower tapered portion 60 and an upper tapered portion 61, the two tapered portions being separated by a stop shoulder 62. The taper of the body 58 complements the inclination of the surfaces 50 and 52 of the members 48 and 49. The body 58 normally occupies a position in which its upper end projects beyond the upper ends of the members 48 and 49. The spring 41, together with the inclination of the surfaces 50 and 51 maintains the body in the projected position, but does not prevent axial movement of the body.

To condition the apparatus for operation one end of a line or cable 63 is threaded through the connecting rod 2 from the upper end of the latter. The line extends beyond the lower closure 5 and is provided with a knot or other stop (not shown) to prevent return movement of the line through the rod, thereby enabling the line 63 to support the entire apparatus. The latch part 19 at the upper end of the rod 2 is fitted into the recess R between the members 26 and 27 so that the enlargement 19 is trapped between the plate 14 and the overhanging shoulders 39 and 40. See FIG. 1. The opening between the notches 37 and 38 accommodates the cable 63, but has a diameter less than that of the enlargement 19. The closure 12 thus is supported by the enlargement 19 of the member 2.

When the closure 12 is supported by the enlargement 19, the entire sampling apparatus may be suspended from the line 63, whereupon the body 1 will be supported by means of the tether chains 21 at a fixed distance below the closure 12 and the closure 5 will be supported by the rod 2 at a fixed distance below the lower end of the body 1. In these positions of the parts, both ends of the sampler body are open and the sampling apparatus may be lowered to any desired depth in a body of water.

When the sampler has been lowered to a predetermined depth, a weighted, annular messenger 64 may be fitted onto the upper end of the cable 63 and permitted to fall. As the messenger falls, it will be guided by the cable so as to enable the messenger to engage the operating member 57 and displace it axially of the motion transmitting members 48 and 49. As the operating member 57 moves axially of the members 48 and 49, the body will exert a transverse or wedging force on the members 48 and 49 and simultaneously move them away from one another, against the biasing force of the spring 41, thereby enlarging the opening defined by the notches 37 and 38. When the diameter of such opening is equal to or greater than the diameter of the latch 19, the weight of the closure 12 will cause the latter to fall toward the upper end of the sampling body 1. As the closure 12 falls, the body 1 also will fall toward the closure 5 until such time as the latter seats in the lower end of the body 1. Following seating of the closure 5 in the lower end of the sampling body, the closure 12 will seat in the upper end of the body, thereby sealing both ends of the sampling body. The sampling apparatus then may be hoisted by means of the cable 63.

Following transverse movement of the clasp members 26 and 27 to their latch releasing positions, the spring 41 will effect return movement of the latch members toward one another, thereby displacing the operating member 57 upwardly. The operating member will be retained in the chamber 52, however, by engagement of the stop flanges 53 and 54 with the stop shoulder 62. To facilitate return movement of the clasp members toward one another, the taper of the body 58 should form a relatively large angle, such as 20°, to the vertical.

Regardless of the angle to which the sampler may be tilted due to a current or the like, the messenger 64 will engage the operating member 57 so as to displace the latter axially of the sampler. Due to the complemental inclination of the side of the operating member and the surfaces 50 and 51 of the respective motion transmitting members, such displacement of the operating member will effect simultaneous movement of the clasp members out of latching engagement with the latch 19. Thus, failure of the latch mechanism to be released is greatly minimized.

Inasmuch as transverse movement of the clasp members out of latching engagement results from axial movement of the operating member 57, rather than from engagement between the messenger and the motion transmitting members 48 and 49, the latter are not subjected to stresses generated by forcible engagement between them and the messenger. Consequently, the force transmitting members can be formed of moldable plastics materials, such as polyurethene, and constitute an integral part of the clasp members, thereby providing for manufacturing economies. The operating member 57 also can be molded from similar plastics materials if desired.

An advantage of the external garter spring 41, apart from the ease from which it may be assembled with the other parts of the mechanism, is that it will retain the clasp members 26 and 27 in assembled relation even though one or both of the motion limiting pins 44 and 45 should be broken. The likelihood of breakage of the pins can be minimized, however, if axial downward movement of the operating body 58 is limited by ledges 65 and 66 formed on the members 48 and 49 and on which the body 58 may seat.

The disclosed embodiment is representative of the presently preferred form of the invention, but is intended to be illustrative rather than definitive thereof. The invention is defined in the claims.

We claim:
1. Latch releasing mechanism for a water sampler or the like having a latch member movable between latched and unlatched positions, said mechanism comprising a pair of clasp members; means mounting said clasp members for movements in directions into and out of latching position; motion transmitting means carried by each of said clasp members for effecting movement of the latter, said motion transmitting means being spaced apart to form a chamber therebetween; operating means; and means supporting said operating means in said chamber for movement along a path transverse to the directions of movement of said clasp members, said motion transmitting means and said operating means being so configured that movement in one direction along said path of said operating means effects movement of said clasp members from said latched position toward said unlatched position.

2. A mechanism according to claim 1 including resilient means acting on said clasp members and yieldably biasing the latter toward said latching position.

3. A mechanism according to claim 2 wherein said resilient means comprises an endless spring encircling said clasp members.

4. A mechanism according to claim 1 wherein said motion transmitting means are spaced from one another and wherein said operating means is interposed between said motion transmitting means.

5. A mechanism according to claim 4 wherein said motion transmitting means have inclined confronting surfaces.

6. A mechanism according to claim 1 wherein said operating means is tapered to complement the inclined surfaces of said motion transmitting means.

7. A mechanism according to claim 1 wherein said operating means projects beyond said motion transmitting means.

8. A mechanism according to claim 1 wherein said motion transmitting means are spaced from one another and said operating means is interposed between said motion transmitting means, said motion transmitting means and said operating means having cooperable stop means for preventing movement of said operating means from between said motion transmitting means.

9. A mechanism according to claim 1 including motion limiting means engageable by said clasp members for limiting movement of the latter out of said latching position.

10. In a release mechanism for a latch member movable from a latched to an unlatched position under the control of a generally downwardly movable weighted messenger and having a support on which is mounted a pair of clasp members movable into and out of latching position, of motion transmitting member carried by and projecting from each of said clasp members for effecting movement of the latter, said motion transmitting members having spaced apart confronting surfaces forming a chamber, the improvement comprising operating means occupying said chamber in a position to be engaged by said messenger, said operating means being movable in said chamber relatively to said motion transmitting means in response to engagement by said messenger and in a direction transverse to the direction of movement of said motion transmitting means, said operating means and said surfaces having complementary configurations such that movement in said one direction of said operating means relative to said motion transmitting members effects movement of said clasp members from said latched position toward said unlatched position.

11. A mechanism according to claim 10 wherein the confronting surfaces of said motion transmitting members are inclined to one another.

12. A mechanism according to claim 11 wherein said operating means is tapered complementally to the inclination of said confronting surfaces.

13. A mechanism according to claim 10 including cooperable stop means on said motion transmitting members and said operating means for preventing movement of the latter out of said chamber.

14. A mechanism according to claim 13 wherein said limiting means comprises a flange on each of said motion transmitting members and a shoulder on said operating means engageable with the flanges on said motion transmitting means.

15. A mechanism according to claim 10 wherein said operating means projects out of said chamber beyond said motion transmitting member.

16. A mechanism according to claim 10 including resilient means yieldably biasing said clasp members toward said latching positions.

17. A mechanism according to claim 10 including motion limit means reacting between said support and said clasp members for limiting movement of the latter out of said latching positions.

18. A mechanism according to claim 10 wherein said motion transmitting members are formed of non-metallic material.

* * * * *

UNITED STATES PATENT AND TRADEMARK OFFICE
CERTIFICATE OF CORRECTION

PATENT NO. : 4,027,538
DATED : June 7, 1977
INVENTOR(S) : Robert P. Snyder - Edmund P. Deja It is certified that error appears in the above-identified patent and that said Letters Patent are hereby corrected as shown below:

Column 6, line 11, after "claim" change "1" to --5.

Signed and Sealed this twenty-third Day of August 1977

[SEAL]

Attest:

RUTH C. MASON
Attesting Officer

C. MARSHALL DANN
Commissioner of Patents and Trademarks